US011135079B2

(12) United States Patent
Kazaryan et al.

(10) Patent No.: US 11,135,079 B2
(45) Date of Patent: Oct. 5, 2021

(54) BRACES FOR ALLEVIATING COMPRESSION AND METHODS OF MAKING AND USING THE SAME

(71) Applicants: Movses Kazaryan, Burbank, CA (US); Lusine Pashikyan, Burbank, CA (US)

(72) Inventors: Movses Kazaryan, Burbank, CA (US); Lusine Pashikyan, Burbank, CA (US)

(*) Notice: Subject to any disclaimer, the term of this patent is extended or adjusted under 35 U.S.C. 154(b) by 455 days.

(21) Appl. No.: 15/981,317

(22) Filed: May 16, 2018

(65) Prior Publication Data
US 2019/0240053 A1    Aug. 8, 2019

Related U.S. Application Data

(60) Provisional application No. 62/625,977, filed on Feb. 3, 2018.

(51) Int. Cl.
*A61F 5/01*    (2006.01)
*A61F 5/02*    (2006.01)
(Continued)

(52) U.S. Cl.
CPC .............. *A61F 5/01* (2013.01); *A61F 5/0102* (2013.01); *A61F 5/0109* (2013.01);
(Continued)

(58) Field of Classification Search
CPC ........ A61F 5/01; A61F 5/0102; A61F 5/0109; A61F 5/0111; A61F 5/0118; A61F 5/0123; A61F 5/0127; A61F 5/013; A61F 5/02; A61F 5/022; A61F 5/024; A61F 5/028; A61F 5/042; A61F 5/055; A61F 2005/0155; A61F 2005/0179; A61F 2005/0197; A61F 5/05883; A61H 1/02; A61H 1/0218; A61H 1/0292; A61H 1/0296; A61H 2201/1604;
(Continued)

(56) References Cited

U.S. PATENT DOCUMENTS 4,721,102 A * 1/1988 Pethybridge ............ A61F 5/024
602/19
5,213,094 A   5/1993 Bonutti
(Continued)

FOREIGN PATENT DOCUMENTS

AU         200179406 A      4/2002
WO    WO-2016134103 A1 *  8/2016  ............... A61H 3/00

OTHER PUBLICATIONS

International Search Report and Written Opinion; PCT International Searching Authority/US dated Apr. 11, 2019; International Application No. PCT US2019/015905; 11 pages; International Searching Authority/ United States, Commissioner for Patents; Alexandria, Virginia.

*Primary Examiner* — Ophelia A Hawthorne
*Assistant Examiner* — Daniel A Miller
(74) *Attorney, Agent, or Firm* — Andrew D. Fortney; Central California IP Group, P.C.

(57) ABSTRACT

A brace including (i) two or more supports configured to contact body parts on opposite sides or ends of one or more joints when the brace is in use and (ii) one or more force application mechanisms that apply a controllable force to the supports in opposite directions to alleviate compression in the one or more joints is disclosed. Methods of manufacturing the brace and of alleviating compression in one or more joints using the brace are also disclosed.

17 Claims, 11 Drawing Sheets

(51) Int. Cl.
*A61F 5/042* (2006.01)
*A61F 5/055* (2006.01)

(52) U.S. Cl.
CPC .......... *A61F 5/0111* (2013.01); *A61F 5/0118* (2013.01); *A61F 5/02* (2013.01); *A61F 5/024* (2013.01); *A61F 5/042* (2013.01); *A61F 5/055* (2013.01); *A61F 2005/0155* (2013.01); *A61F 2005/0179* (2013.01); *A61F 2005/0197* (2013.01)

(58) Field of Classification Search
CPC .... A61H 2201/1609; A61H 2201/1614; A61H 2205/04
USPC .............. 602/5, 19, 12, 16, 18; 128/874
See application file for complete search history.

(56) References Cited

U.S. PATENT DOCUMENTS

| | | | |
|---|---|---|---|
| 5,256,135 A | 10/1993 | Avihod | |
| 5,462,518 A * | 10/1995 | Hatley | A61F 5/024 482/124 |
| 7,445,608 B2 * | 11/2008 | Dunfee | A61F 5/024 128/845 |
| 8,932,244 B1 * | 1/2015 | Besancon | A61F 5/042 602/19 |
| 10,322,023 B1 * | 6/2019 | Ramadan | A61F 5/042 |
| 2004/0144334 A1 | 7/2004 | Berardo | |
| 2006/0149178 A1 * | 7/2006 | Dunfee | A61F 5/024 602/19 |
| 2007/0156074 A1 * | 7/2007 | Cojbasic | A61F 5/026 602/19 |
| 2013/0060179 A1 * | 3/2013 | Modglin | A61F 5/01 602/18 |
| 2014/0224258 A1 * | 8/2014 | Krook | A61F 5/56 128/848 |
| 2015/0073322 A1 | 3/2015 | Cohen | |
| 2016/0278962 A1 * | 9/2016 | Zhang | A61F 5/026 |
| 2017/0203432 A1 * | 7/2017 | Andrianesis | A61F 2/583 |
| 2018/0036194 A1 * | 2/2018 | Matthew | A61H 1/0274 |
| 2020/0188222 A1 * | 6/2020 | Duncan | A61H 1/00 |

* cited by examiner

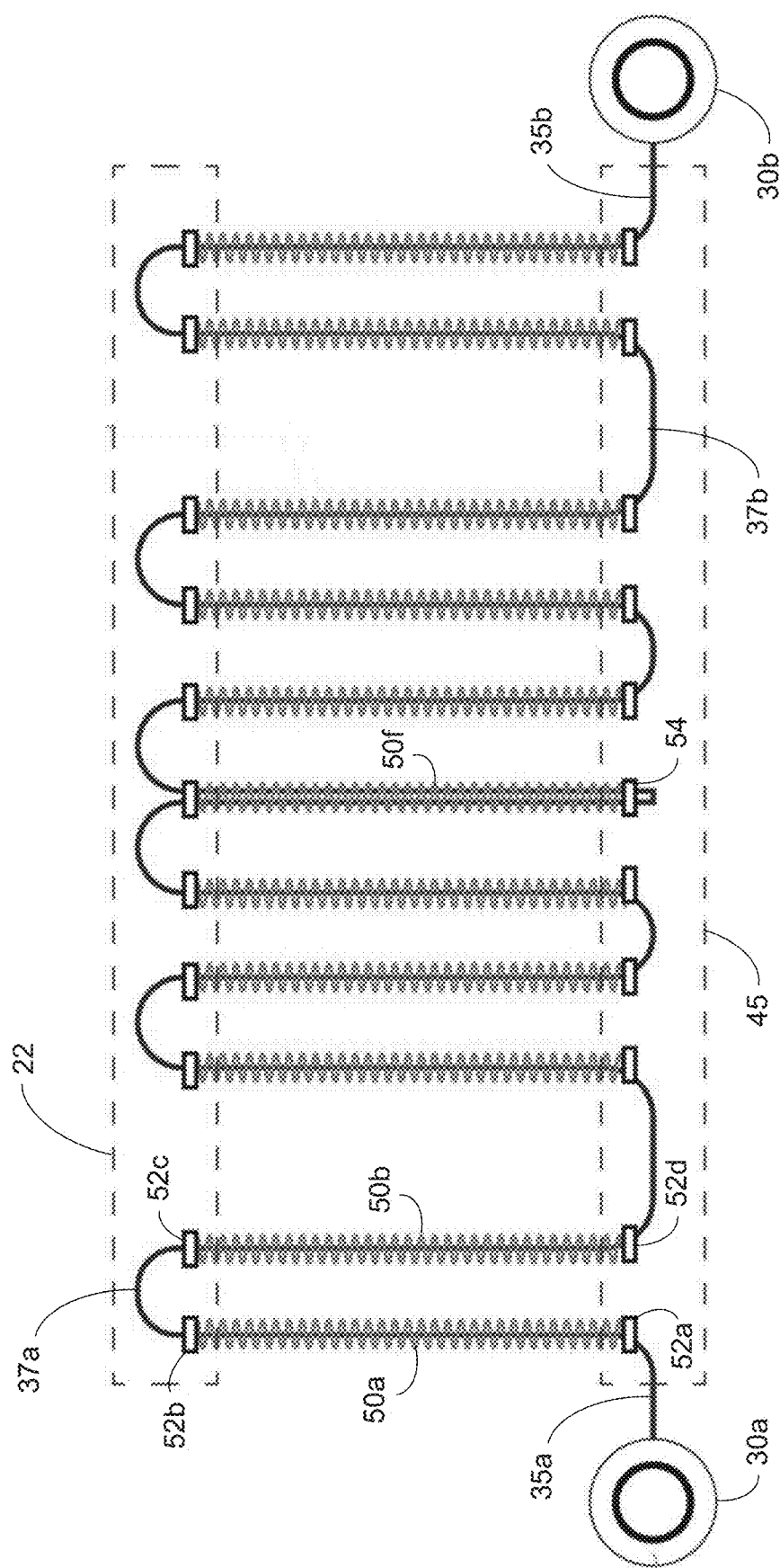

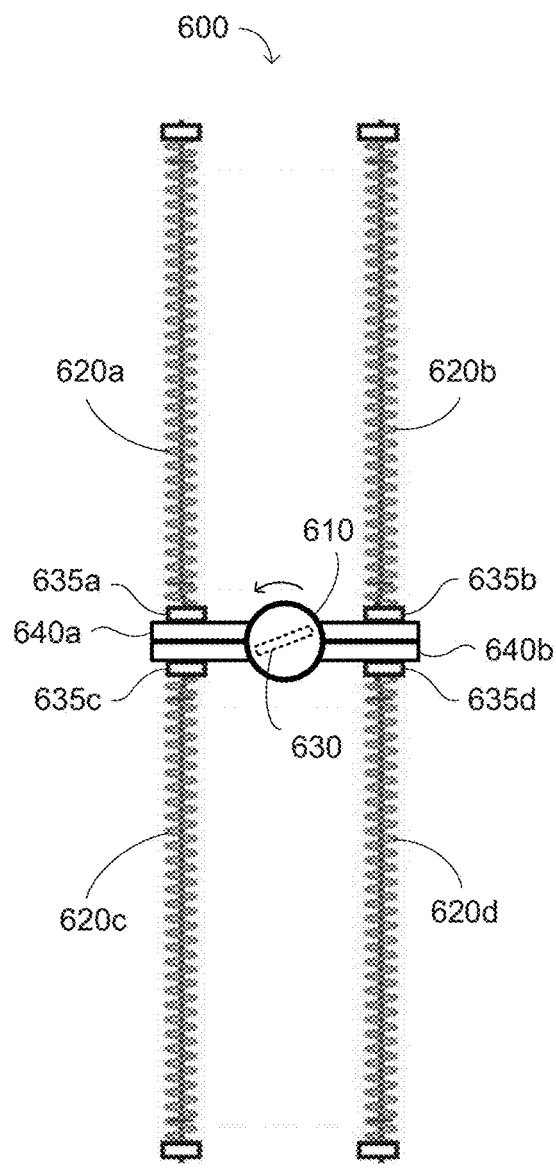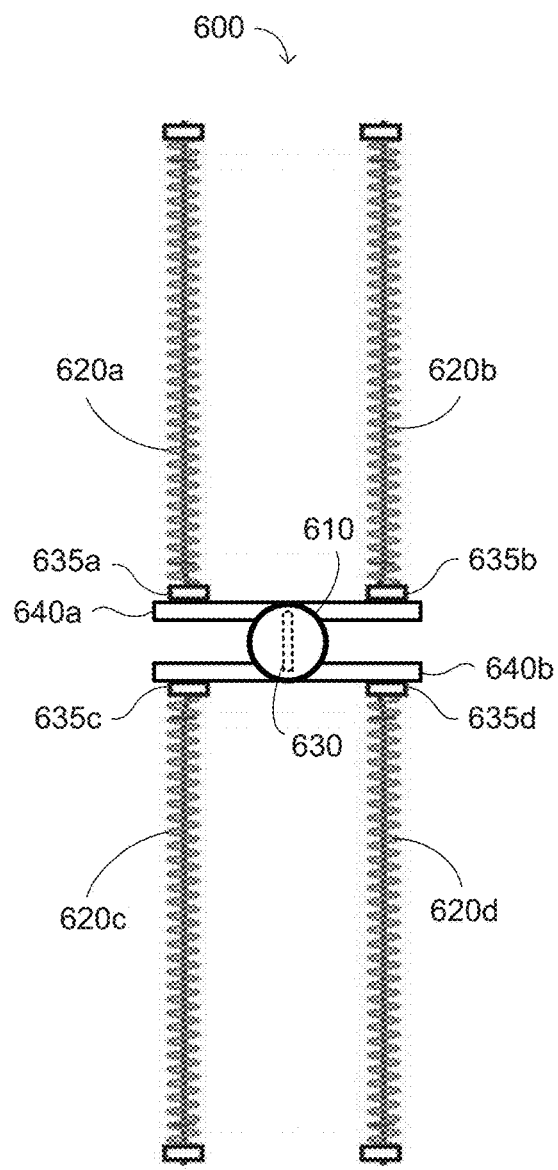

BRACES FOR ALLEVIATING COMPRESSION AND METHODS OF MAKING AND USING THE SAME

CROSS REFERENCE TO RELATED APPLICATION(S)

This application claims the benefit of U.S. Provisional Patent Application No. 62/625,977, filed on Feb. 3, 2018, incorporated herein by reference as if fully set forth herein.

FIELD OF THE INVENTION

The present invention generally relates to the field of medical braces, especially for body parts and joints. More specifically, embodiments of the present invention pertain to a brace that applies a force in opposite directions along or across the body part or joint and that can be adjusted to alleviate pain or discomfort, and methods of making and using the same.

DISCUSSION OF THE BACKGROUND

Joint pain is a problem for many people due to deterioration of or injury to a joint in the human body over time. A main cause of joint pain and joint deterioration is the compression of the cartilaginous material in the joint. While the deleterious effects of joint compression may be inevitable, everyday activities like manual labor, playing sports, and simply gravity can exacerbate the condition.

A common, minimally invasive way to treat joint pathology is through the use of a brace. Braces may be fastened around an appendage or the torso. For example, a brace may be fastened around or secured to the arm to treat elbow pain or injury. A different brace may be fastened around or secured to the leg to treat knee pain or injury, and still another brace may be fastened around or secured to the torso to treat pain or injury along the spine. Most braces for joints are designed to fit tightly around a particular joint. While this design may stabilize a weak joint, it may also further compress the joint. Therefore, traditional braces may not relieve joint pain or prevent further joint degeneration as much as desired, due at least in part to joint and/or cartilage compression.

Currently, there are not many widely-practiced treatments other than surgery for alleviation of joint pain that focus on ways to relieve joint compression or reverse the forces that lead to or cause joint compression. This is particularly challenging because normal activities such as walking and sitting upright, along with gravity, naturally keeps most joints and the cartilage in these joints in a state of constant compression. For instance, a major cause of back pain is the compression of the vertebral discs that act as shock absorbers between spinal bones.

This "Discussion of the Background" section is provided for background information only. The statements in this "Discussion of the Background" are not an admission that the subject matter disclosed in this "Discussion of the Background" section constitutes prior art to the present disclosure, and no part of this "Discussion of the Background" section may be used as an admission that any part of this application, including this "Discussion of the Background" section, constitutes prior art to the present disclosure.

SUMMARY OF INVENTION

Relieving the tension and compression on joints advantageously lessens pain, increases mobility, and reduces joint deterioration over time. Decreasing the pressure on the discs between bones in the spine advantageously alleviates back pain and can be a long-term solution to both back pain and decreased mobility of the spine.

The present invention pertains to an apparatus that is worn around a torso, knee, elbow, neck, etc., that utilizes opposing forces applied to supports along, or on either side of, a joint or body part to reduce or relieve joint compression and oppose the force of gravity. This reduces joint compression and decreases tension in or on the joint. As the joints are decompressed through the use of the present brace over time, joint pain may decrease and mobility may increase. The present apparatus may provide a long-term solution for many people who suffer chronic joint pain due to joint compression. The present apparatus may also be used preventatively by people who anticipate joint pain in the future, as it may slow joint degeneration in individuals at risk for developing certain types of joint disease (e.g., arthritis).

Many braces are bulky and/or cumbersome, while providing insufficient or minimal relief to the joints they target. The present invention advantageously provides greater relief to the targeted joint(s) through the use of springs or other mechanisms that apply opposing forces to supports on opposite sides of the targeted joint(s), and that can be adjusted (e.g., by the user) to achieve greater comfort. The present brace is generally less bulky than traditional braces, enabling daily use, during a multitude of activities. Individuals with chronic back pain, athletes, and those who spend long hours at a desk or driving a vehicle may find long-term relief from use of the present brace.

In particular, the present invention relates to a brace comprising two or more supports and one or more force application mechanisms that apply a controllable force to the supports in opposite directions. The supports are configured to contact body parts on opposite sides or ends of one or more joints when the brace is in use. The controllable force alleviates compression in the joint(s).

In some embodiments, the force application mechanism(s) comprise a plurality of springs or coils coupled to or connected between (i) at least a first one of the supports on a first side or end of the joint(s) and (ii) at least a second one of the supports on a second side or end of the joint(s), opposite from the first side or end. The apparatus may further comprise a tension control mechanism configured to change or maintain a tension of each of the coils or springs. The coils attach to a central eyelet which acts as an anchor.

In one set of examples, the tension control mechanism comprises one or more wires or cables through the springs or coils (in parallel and/or in series), and at least one knob or strap operably connected to the wire(s) or cable(s). Each knob or strap is configured to control a length of the wire(s) or cable(s). When two or more wires or cables are through the springs or coils, the wires or cables may run through the springs or in parallel and/or in series. In a brace configured to relieve compression on the spine, there may be first and second knobs on each side of the abdominal area. The knobs are configured to control the tension of the coils or springs (e.g., to the wearer's comfort level). Alternatively, the tension control mechanism may comprise one or more actuators configured to change or maintain a length of at least one of the springs, and a motor operably connected to and configured to control a position of the corresponding actuator(s).

The apparatus may further comprise a cover configured to secure a position of each of the supports in the brace. The cover may be further configured to enclose the force application mechanism(s) (e.g., the springs or coils). Enclosing the force application mechanism(s) may protect both (i) the wearer from potential injury and (ii) the force application mechanism(s) from potential damage. The apparatus also may further comprise a cushion or padding covering at least part of each of the supports, and optionally, enclosed by the cover. The cushion or padding may be configured to distribute the controllable force across a larger area of the body part(s) contacted by a corresponding support.

The present brace may be adapted for use on a person's back (e.g., stylized as a vest), knee or elbow (e.g., stylized as a sleeve), neck (e.g., stylized as a collar), etc. In the vest, there may be two support regions, one around the waist (which may be covered by or which may overlap with a belt configured to fasten, tighten and/or secure the vest around the person's waist), and a second one under the arms (e.g., around the thorax). The cover may comprise one or more different materials, such as poly(para-phenylene terephthalamide) (e.g., KEVLAR®, commercially available from E. I. du Pont de Nemours and Company, Wilmington, Del.) or graphene (e.g., for military applications), neoprene (e.g., for waterproofing), polytetrafluoroethylene (e.g., GORE-TEX®, commercially available from W. L. Gore & Associates, Inc., Newark, Del.; for use in wet or humid climates), Spandex (for a close/snug fit), etc. The brace may further include a heating mechanism (e.g., one or more resistive wires and a source of electrical power, such as a battery), a massaging mechanism (e.g., a disc or orb configured to rotate around an offset axis and a motor configured to rotate the disc or orb), sealable pockets (e.g., in which to place one or more cold packs for cryotherapy), etc.

These and other advantages of the present invention will become readily apparent from the detailed description of various embodiments below.

BRIEF DESCRIPTION OF THE DRAWINGS

FIG. 2 is a diagram of an exemplary coil mechanism suitable for use in the exemplary vest of FIG. 1, in accordance with one or more embodiments of the present invention.

FIGS. 11A-B show an exemplary mechanism for modifying the compression on a set of springs or coils in accordance with one or more embodiments of the present invention.

DETAILED DESCRIPTION

Figure 1:
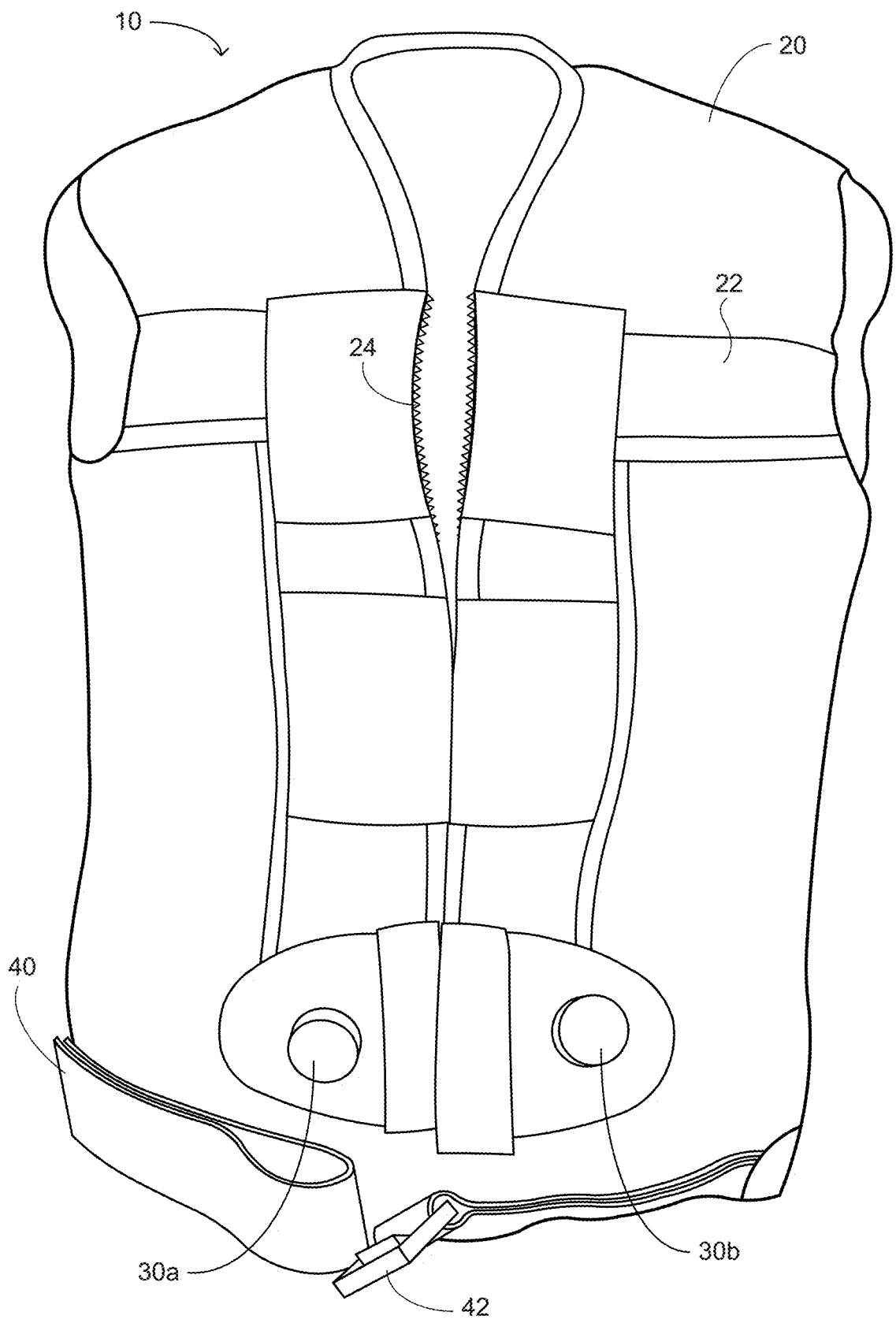
FIG. 1 shows an exemplary vest brace, in accordance with embodiments of the present invention.

Reference will now be made in detail to various embodiments of the invention, examples of which are illustrated in the accompanying drawings. While the invention will be described in conjunction with the following embodiments, it will be understood that the descriptions are not intended to limit the invention to these embodiments. On the contrary, the invention is intended to cover alternatives, modifications and equivalents that may be included within the spirit and scope of the invention as defined by the appended claims. Furthermore, in the following detailed description, numerous specific details are set forth in order to provide a thorough understanding of the present invention. However, it will be readily apparent to one skilled in the art that the present invention may be practiced without these specific details. In other instances, well-known methods, procedures, components, and circuits have not been described in detail so as not to unnecessarily obscure aspects of the present invention.

The technical proposal(s) of embodiments of the present invention will be fully and clearly described in conjunction with the drawings in the following embodiments. It will be understood that the descriptions are not intended to limit the invention to these embodiments. Based on the described embodiments of the present invention, other embodiments can be obtained by one skilled in the art without creative contribution and are in the scope of legal protection given to the present invention.

Furthermore, all characteristics, measures or processes disclosed in this document, except characteristics and/or processes that are mutually exclusive, can be combined in any manner and in any combination possible. Any characteristic disclosed in the present specification, claims, Abstract and Figures can be replaced by other equivalent characteristics or characteristics with similar objectives, purposes and/or functions, unless specified otherwise. Furthermore, it should be understood that the possible permutations and combinations described herein are not meant to limit the invention. Specifically, variations that are not inconsistent may be mixed and matched as desired.

The terms "vest," "brace," and "vest brace" may be used interchangeably but these terms are also generally given their art-recognized meanings. In addition, the terms "part," "portion," and "region" may be used interchangeably but these terms are also generally given their art-recognized meanings. Furthermore, the terms "connected to," "in connection with," and grammatical variations thereof include both direct and indirect connections, unless the context of its use clearly indicates otherwise. Also, unless indicated otherwise from the context of its use herein, the terms "known," "fixed," "given," "certain" and "predetermined" generally refer to a value, quantity, parameter, constraint, condition, state, process, procedure, method, practice, or combination thereof that is, in theory, variable, but is typically set in advance and not varied thereafter when in use.

The term "length" generally refers to the largest dimension of a given 3-dimensional structure or feature. The term "width" generally refers to the second largest dimension of a given 3-dimensional structure or feature. The term "thickness" generally refers to a smallest dimension of a given 3-dimensional structure or feature. The length and the width, or the width and the thickness, may be the same in some cases.

An Exemplary Vest Brace

FIG. 1 shows an exemplary vest brace 10 designed to be worn over a person's torso. The material 20 of the vest brace 10 may be specific to a particular use or embodiment of the vest brace 10. Examples of suitable materials 20 include Kevlar®, neoprene, canvas, cotton, acrylic, Spandex, etc. The vest brace 10 includes an upper support region 22 that secures an upper support around the wearer's upper torso (e.g., under the arms). The upper support region 22 may be defined by stitching above and below the upper support to secure the upper support to the vest brace 10. Alternatively, the upper support may be secured to the vest brace 10 using adhesive, rivets, pins, other fasteners, combination(s) thereof, etc. The upper support region may further include one or more pockets or compartments sewn onto the front of the vest brace 10. However, such pockets or compartments may be located elsewhere in the vest brace 10 (e.g., generally on or in the front or sides of the vest brace 10) and/or may be formed or attached to vest brace 10 by other techniques (e.g., using rivets, staples, hook-and-loop fasteners, etc.).

The vest brace 10 includes a belt or strap 40 that fastens the vest brace 10 around the wearer's abdomen. The belt or strap 40 can be fed through a buckle 42 and secured to itself by a hook-and-loop (e.g., Velcro®) fastener, but other fastening and/or tightening mechanisms are also possible, such as a prong that inserts into a hole, a plastic buckle with fins, etc. Alternatively, the vest brace 10 may include strings or laces (e.g., that may be tied) to secure the vest brace 10 to the wearer's body. The belt or strap 40 may overlap and/or conceal a lower support region of the vest brace 10. Alternatively, the belt or strap 40 may function as an additional support or brace.

The lower support region may be defined by stitching above and below the lower support to secure the lower support to the vest 10. Alternatively, the lower support may be secured to the vest brace 10 using adhesive, rivets, pins, other fasteners, combination(s) thereof, etc. The lower support region may also include one or more pockets or compartments sewn onto the front of the vest brace 10. The upper and lower supports may be the same or different from each other, and may comprise one or more materials having a relatively high modulus of elasticity or Young's modulus (e.g., 0.1 GPa or higher), such as high-density polyethylene, a polycarbonate, polytetrafluoroethylene (e.g., Teflon™) or another hard plastic, a hard rubber, wood, a ceramic, a metal, etc. A single support in each of the upper and lower support regions may circumscribe substantially the entire torso, or separate left and right supports can contact the person's torso under the left and right arms and above the left and right hips. Separate supports in each support region can be further secured in place using vertical stitching on each side of the support.

The vest 10 may be fastened in the center by a zipper 24 or other fastening device (e.g., buttons, hooks and loops [Velcro®], etc.). The zipper 24 is fastened to the vest brace 10 by stitching. The vest 10 includes two knobs 30a/30b that in some embodiments are mirror images of one another and that may act as control knobs to increase or decrease the tension of the coils in the vest brace 10. The knobs 30a/30b are located in the abdominal region of the vest, one on each side of the midline. Alternatively, a cord or wire that slides through a resealable clamp on the outside of the vest brace 10 may increase or decrease the tension of the coils. Pulling the cord or wire away from the vest brace 10 may increase the tension in the coils, and thus, decrease the force on the upper and lower supports, and allowing the cord or wire to retract in the opposite direction (e.g., into the vest brace 10) may decrease the tension in the coils and increase the force on the upper and lower supports.

Figure 12A:
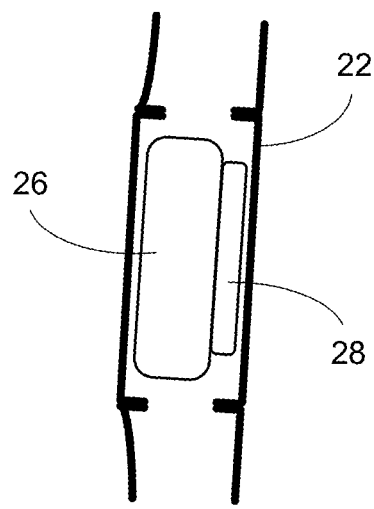
FIGS. 12A-B are cross-sectional diagrams of exemplary supports with padding suitable for use in the exemplary vest of FIG. 1, in accordance with embodiments of the present invention.
Figure 12B:
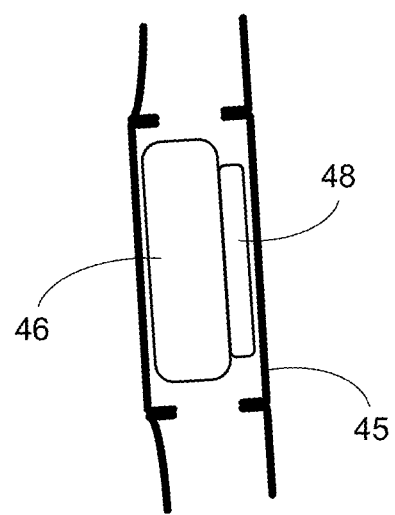

FIG. 2 shows the internal coils or springs 50a-k and tension control mechanism of the vest brace 10 (FIG. 1) in detail. An upper end of each coil or spring 50a-k is secured to a support (not shown) in the upper support region 22 of the vest brace 10, and the opposite (lower) end of each coil or spring 50a-k is secured to a support (not shown) in the lower support region 45. The upper ends of the coils or springs 50a-k are secured to the upper support by recessed eyelets (e.g., 52b/52c) that anchor the coils 50a-k to the upper support. The lower ends of the coils or springs 50a-k are secured to the lower support in the lower support region 45 by similar or identical recessed eyelets (e.g., 52a, 52d and 54). FIG. 12A is a cross-section of the upper support region 22 of the vest brace 10 with a support 28 therein and padding 26 covering the support 28, and FIG. 12B is a cross-section of the lower support region 45 of the vest brace 10 with a support 48 therein and padding 46 covering the support 48.

First and second wires 35a-b respectively run serially through the coils or springs 50a-e and 50g-k and in parallel with each other through the coil or spring 50f. The wires 35a-b also pass through the corresponding eyelets (e.g., 52a-d). The turns or curved portions (e.g., 37a-b) of the wires 35a-b are in the upper and lower support regions 22 and 45. At the lower end of the coil or spring 50f, the wires 35a-b pass through an anchor eyelet 54. The wires 35a-b are secured to at least one of each other, the lower support and an underside of the eyelet 54 to anchor an end of the wires 35a-b to the lower support and to an end of the chain of springs or coils 50a-k. For example, the end of the wires 35a-b below the eyelet 54 may be secured by a bolt, a clamp, a knot, solder, or other fastening method. The anchor eyelet 54 is anchored to the vest by a bolt or other fastening device that can withstand the tension of the coils. Alternatively, the eyelet 54 can be in the upper support region 22.

In another embodiment, two ratchet wheel assemblies (which may be turned with a knob or a key) may be situated on either side of the joint. For example, one ratchet wheel assembly may engage a spring or spring assembly that creates or provides an "upward" force, while the second ratchet wheel assembly creates or provides a "downward" force moving away from the other force (e.g., using the same or a different spring or spring assembly). One end of the tensioning wires 35a-b may be attached to the ratchet wheels and/or control knobs 30a/30b with an adhesive (e.g., epoxy) or a fastener. The other end of the tensioning wires 35a-b may be fed through openings or eyelets in the opposing upper and lower supports (e.g., outside of the springs or coils 50a-k), drawn in or fed through the spring or spring assembly, and tethered to a bushing on either side of the joint. As the ratchet wheel is turned, the tensioning wire becomes taut, and with each turn or partial turn, the bushing pushes against the spring or spring assembly that forces the support "upward" and away from the joint. The lower ratchet wheel is then actuated (e.g., turned) to drive the spring or spring assembly "downward" and away from the joint opposite the force of the upper ratchet wheel. Each ratchet wheel assembly may be adjusted until a desired comfort level is achieved. Some alternative embodiments include a single ratchet wheel that is adjusted, while the other assembly is replaced with an anchor point that is not adjusted at all.

FIG. 2 also shows the control knobs 30a-b around which the wires 35a-b are wrapped. The knobs 30a-b cause the coils 50a/50b to contract or shorten when rotated in a first direction (e.g., counter-clockwise for the knob 30a and clockwise for the knob 30b) and extend or lengthen when rotated in the opposite direction. When the wires 35a-b are contracted or shortened, the force that the upper and lower supports applies to the person's torso (under the left and right arms and above the left and right hips) decreases. Conversely, when the wires 35a-b are extended or lengthened, the force that the upper and lower supports applies to the person's torso increases. The control knobs 30a-b may comprise conventional latching or locking rotary knobs to which an end of each wire 35a-b can be secured. The control knob 30b may be a mirror image of the control knob 30a.

A further embodiment of the control knob 30a-b may comprise a ratchet-and-key type of design. The "ratchet" wheel may comprise a plurality of slotted teeth or apertures (e.g., at least 4, 6, 8, 10, 12, 16, 20 or more teeth or apertures) and may be molded or extruded from a small piece of material (e.g., plastic or metal). The wheel is then sewn or fastened into a recessed pocket above or below the coils 50 of the brace 10. The tensioning wires 35a-b may be attached to the wheel via an adhesive (e.g., epoxy) or a fastener. The "key" may comprise another molded or extruded piece of material (e.g., plastic or metal) with key slots that run longitudinally down the barrel. The barrel may have a length about equal to or slightly less than the length of the teeth or depth of the apertures of the ratchet wheel. When the key is inserted into the wheel, the apertures and key slots should be flush (e.g., mate with and/or be complementary to each other) so that upon turning, the key can tighten or loosen the tensioning wires 35a-b. When the desired comfort/tension level is reached, the wheel is locked into place and the key is removed. The key can then be used to adjust the other ratchet wheel on the opposite side of the brace. The ratchet wheels may be mirror images of each other, although the same key may turn both ratchet wheels.

Figure 3A:
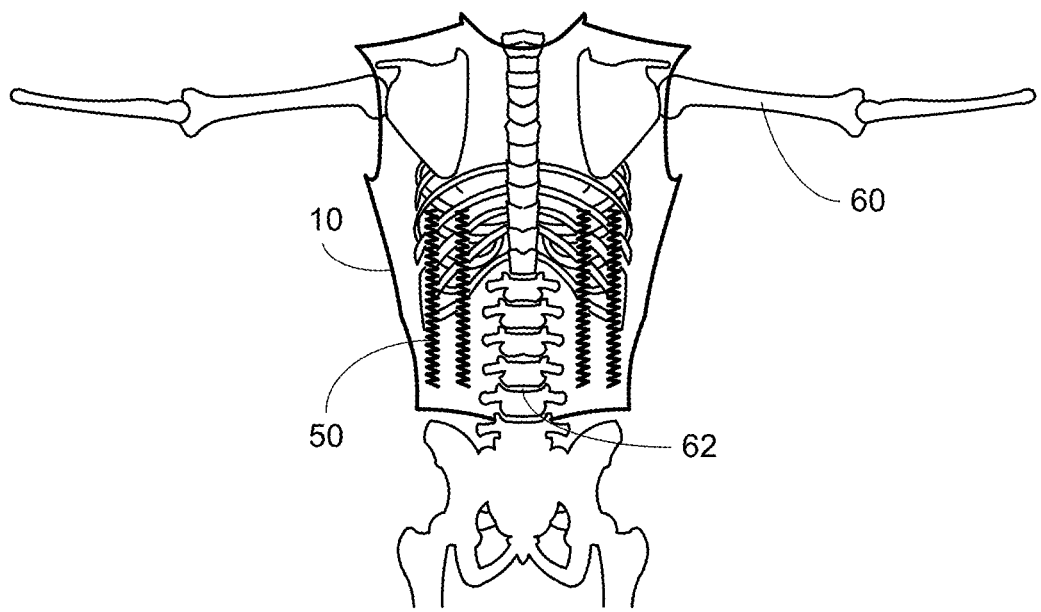
FIG. 3A shows an overlay of a simplified version of the exemplary vest brace shown in FIG. 1 on a human skeleton, indicating the placement of the coils within the vest, in accordance with one or more embodiments of the present invention.
Figure 3B:
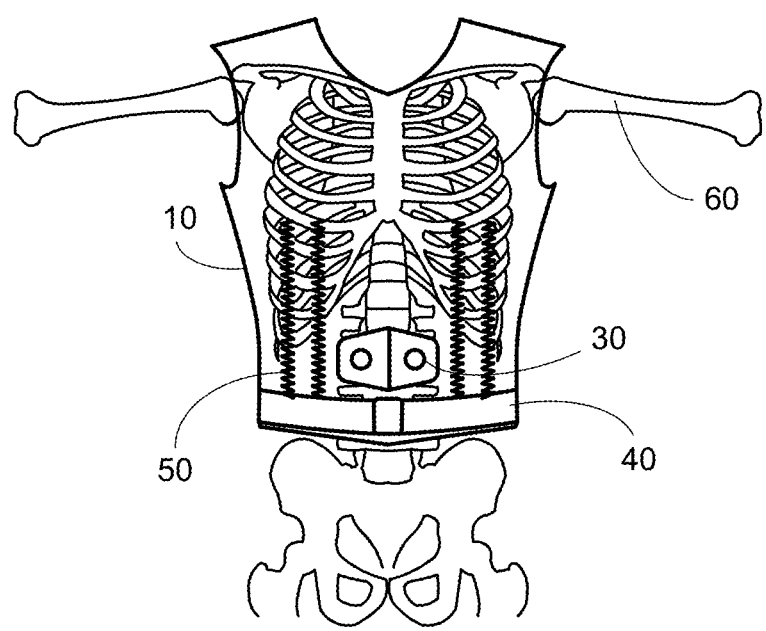
FIG. 3B shows an overlay of a more complex version of the exemplary vest brace on a human skeleton, in accordance with one or more embodiments of the present invention.

FIG. 3A shows an overlay of the vest brace 10 on a human skeleton 60 from the back. FIG. 3B shows an overlay of the vest brace 10 on a human skeleton as seen from the front, indicating the placement of the belt 40, the knobs 30, and the coils 50 of the vest brace 10. The positioning of the coils 50 relative to a person's spine acts to extend the spine when the vest brace 10 is properly engaged and the springs or coils 50 are extended or lengthened. The extension of the spine is achieved by the spring mechanism of the brace and relieves compression of the discs between the vertebrae of the spine when the person wears the vest brace 10, thus alleviating disc pressure by increasing space(s) 62 between the vertebrae (e.g., each of the vertebrae between the upper and lower supports).

Figure 4:
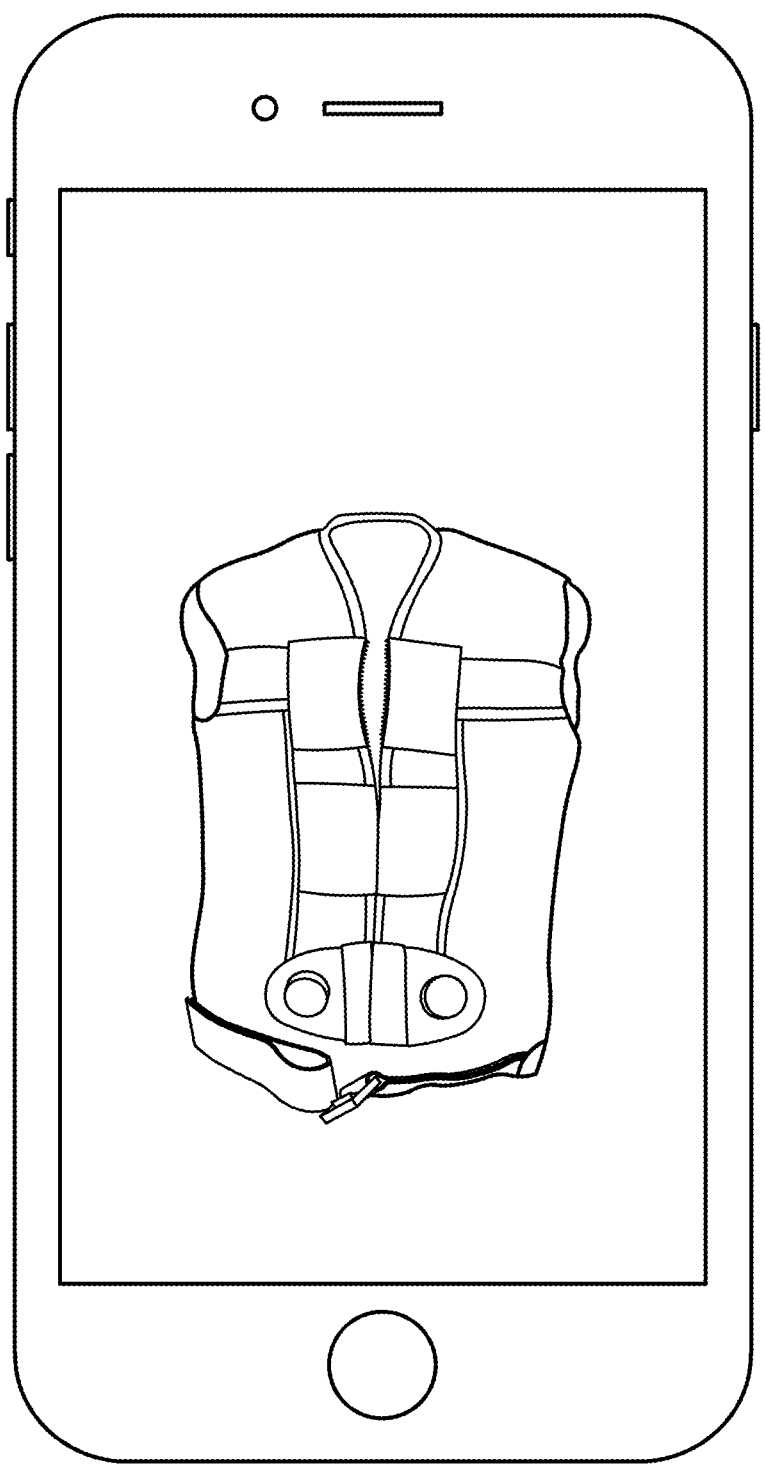
FIG. 4 shows a smart phone displaying an exemplary app that allows for remote control and/or programming of the brace, in accordance with one or more embodiments of the present invention.

FIG. 4 shows a smart phone displaying an app adapted to control and/or program the present brace. The app may include controls such as automated timers and/or programmable schedules that enable the wearer to apply the brace and/or make adjustments in the brace according to a predetermined schedule (e.g., as determined by a health care professional). The app also allows the user to create custom settings for the brace (e.g., coils can be set or adjusted individually, such as in the case of an asymmetrical injury or pain).

The brace may be modified for use in conjunction with the app, and when in use, the tension on and/or force applied by each spring or coil may be adjusted using the app. Various acceptable modifications are described with respect to the hardware examples shown in FIGS. 5A-D.

Figure 5A:
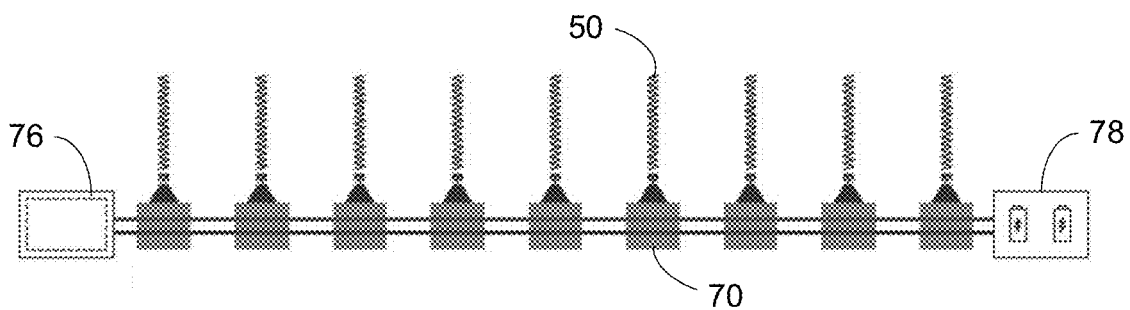
FIGS. 5A-D show exemplary hardware for the remotely controllable and/or programmable brace, in accordance with one or more embodiments of the present invention.
Figure 5B:
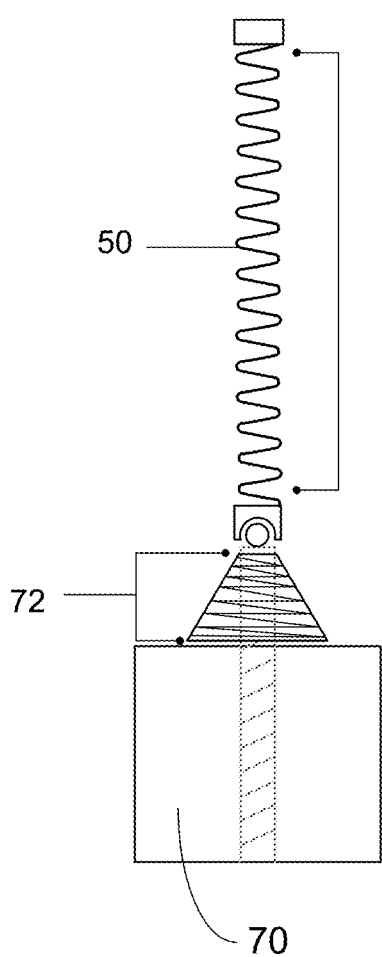
Figure 5C:
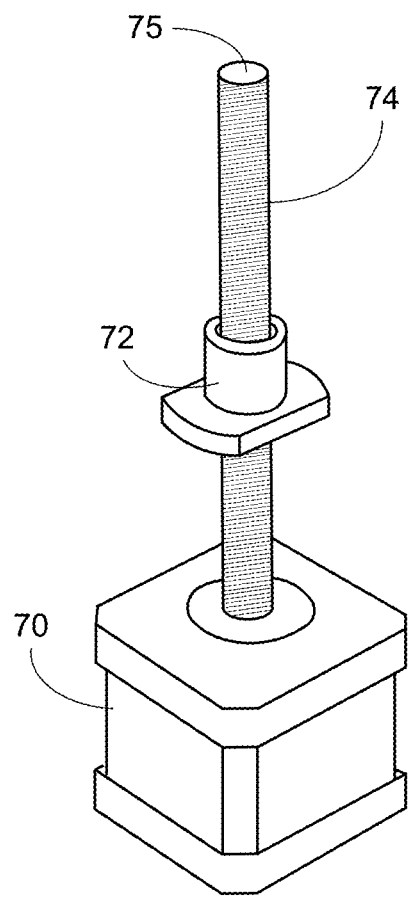
Figure 5D:
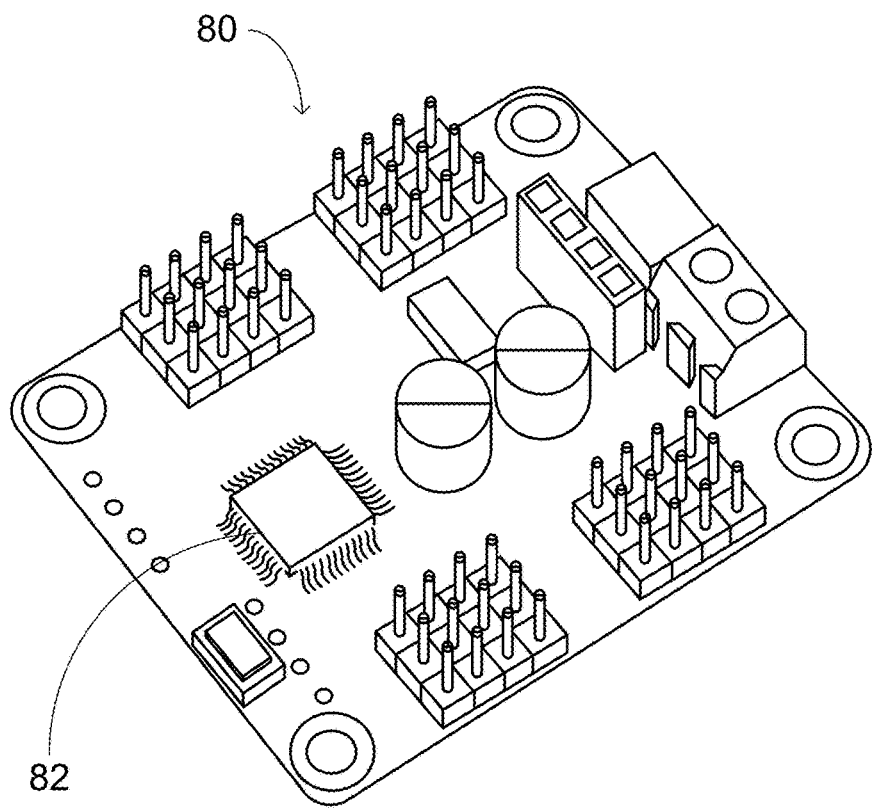

FIG. 5A shows a series of coils or springs 50, which may be anchored to an upper support similarly to the springs or coils in the vest brace 10 (FIG. 1). The lower end of each of the coils or springs 50 is secured to a screw 74 (FIG. 5C) operably connected to a servo motor 70. The screw 74 is connected directly or indirectly through a threaded bracket or fastener 72 (FIG. 5C) to the lower end of the spring or coil 50 (FIG. 5A). Alternatively, the end 75 of the screw 74 may push directly against the bottom of the spring 50. For example, the end 75 of the screw 74 may push against a holder or bracket secured to or surrounding the bottom of the spring 50 and to the lower support (see FIG. 5B) to contract or extend the spring 50. Rotating the screw 74 in one direction (e.g., counter-clockwise) may force the bracket/fastener 72 away from the motor 70, and thus contract the spring 50 and reduce the distance between the upper and lower supports, lessening the force on the body parts in contact with the upper and lower supports. Reversing the rotation direction of the screw extends the spring 50 and increases the distance between the upper and lower supports, thereby increasing the force on the body parts that contact the upper and lower supports.

The modifications in FIG. 5A may also include a smart control module 76 powered by a battery module 78. The servo motors 70 may also be powered by the battery module 78. The smart control module 76 may include a driver board 80 (see FIG. 5D) in the vest that, in conjunction with the servo motors 70, effectively replace the function(s) of the control knobs 30a-b. The driver board 80 may be secured in the vest by stitching or riveting, and may control the servo motors 70, thereby controlling the extension(s) and contraction(s) of the springs. In one embodiment, the driver board 80 may include a wireless transceiver adapted to communicate with the smart phone (e.g., using a Bluetooth protocol). The driver board 80 may have one or more of the following characteristics, functions, and/or parameter values:

Wireless signal transmission and reception

An 8-bit to 32-bit microcontroller 82, running an ARM processor core

Nonvolatile (e.g., flash) memory

An operating frequency of 10-100 MHz (e.g., 48 MHz)

Motor operating voltage of 5V-7.4V and a servo voltage of 5-7V 2-32 Servo motor channels Servo minimum step: 1 us DC motor channels that can include 2 or more external connections to servo motors and/or step motors (which may receive a digital signal)

A motor control frequency of 5-50 KHz (e.g., 25 KHz)

4-16 Analog control channels

A serial (e.g., two-wire) communication interface (e.g., IIC, using TTL logic)

A communication speed of 115200-2400 Kps 2 kb-128 kb static RAM memory (which may be integrated or packaged with the microcontroller)

An Exemplary Elbow Brace

Figure 6:
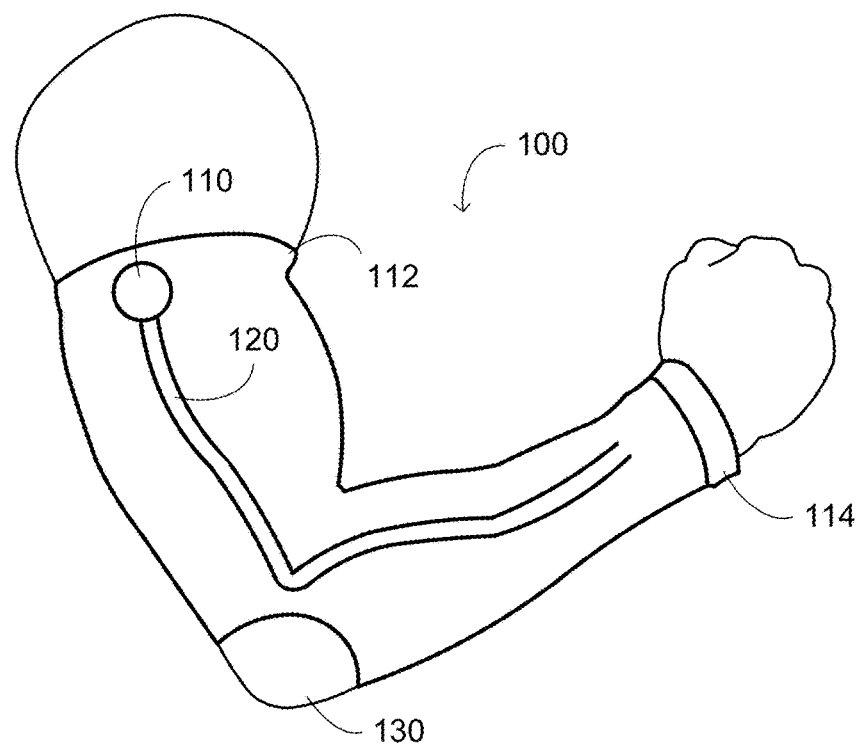
FIG. 6 shows an exemplary elbow brace, in accordance with one or more embodiments of the present invention.

FIG. 6 shows an embodiment 100 of the present brace adapted for a human elbow. The elbow brace 100 includes an upper support region 112 that secures the brace 100 around the upper arm under the shoulder, and that secures and/or contains an upper support (not shown) therein. The upper support may comprise an elastic material. The brace 100 also includes a lower support region 114 that secures the brace 100 to the lower arm around the wrist and contains a lower support (not shown) therein. The brace 100 includes an opening 130 around the elbow to allow for air flow and articulation (e.g., free movement) of the joint when wearing the brace 100, without compressing the elbow. The brace 100 also includes coils 120 within layers of the cover material of the brace 100. The coils 120 may be located across the length of the arm from the upper support region 112 to the lower support region 114. Circumferentially, the coils 120 may be located along a forward-facing and a rearward-facing surface, and/or on inner- and outer-facing surfaces. In some embodiments, a single coil 120 provides sufficient relief from the adverse effects of joint compression, but two or more coils 120 distributes the pressure on the upper and lower supports more evenly than a single coil. The tension of the coils 120 may be adjusted with a control knob 110 located on the upper portion of the brace 100. The control knob 110 may also be located at the wrist end of the coil 120 and/or on the inner surface of the brace 100 (e.g., the surface that faces the torso or to the front of the torso).

The coils 120 control the amount of decompression on the elbow joint by applying opposing forces on the supports in the upper and lower support regions 112 and 114 (e.g., forces that move or push the upper and lower support regions 112 and 114 away from the elbow). However, in this embodiment, the coils 120 should have sufficient flexibility to allow the arm to bend relatively easily at the elbow. The decompression of the elbow joint may improve mobility and alleviate joint pain. The control knob 110 is attached to a wire in each of the coils 120 and allows the user to lengthen or contract the brace 100 to his/her comfort level by turning the control knob 110. The control knob 110 may be attached to the elbow brace 100 with stitching or other conventional fastening.

The material for the cover of the brace 100 may be specific to the particular application of the brace. For example, the cover of the brace 100 may comprise or be made of canvas or neoprene for civilian use, Kevlar® or graphene for military use, etc. In a further embodiment, the elbow brace 100 may have two control knobs 110 and four coils or springs 120. One of the control knobs 110 may control the coils 120 along the upper arm, and the other of the control knobs 110 may control the coils 120 along the lower arm, with each set of the coils 120 anchored to one or more central eyelets in the brace 100 (e.g., in a central support near or adjacent to the elbow). This embodiment allows the coils 120 of the elbow brace 100 to completely traverse the four quadrants of the upper and lower arm, allowing for complete control of the elbow joint through the expansion and/or compression of the coils 120 in the brace 100. This embodiment may include the coils 120 in the medial, lateral, anterior, and posterior portions of the elbow brace 100, and compression on the elbow joint may be controlled minutely using different compression combinations of the above-mentioned coils 120 (e.g., using coils controlled by battery-operated servo motors, similar to those shown in FIGS. 5A-D).

An Exemplary Knee Brace

Figure 7:
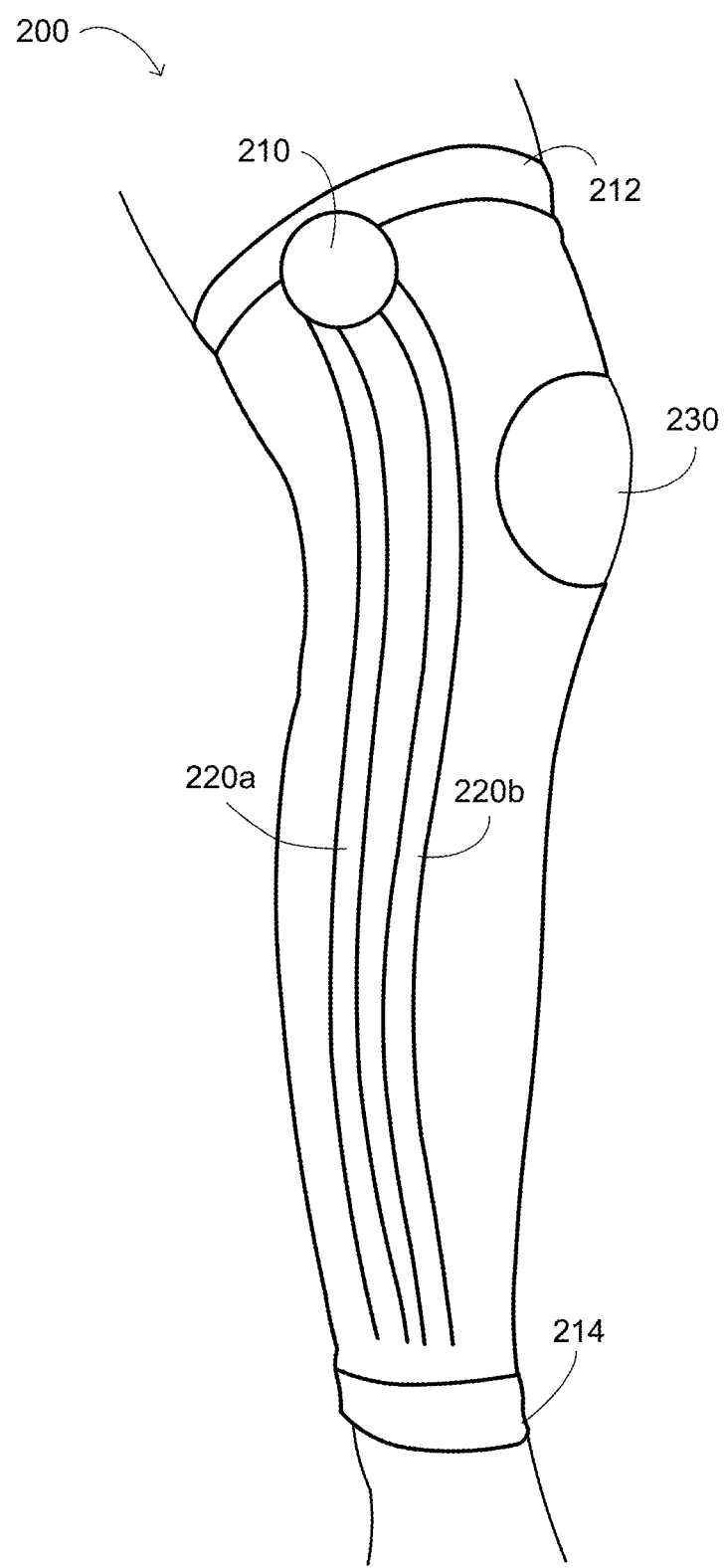
FIG. 7 shows an exemplary knee brace, in accordance with one or more embodiments of the present invention.

FIG. 7 shows an embodiment of a brace 200 adapted for the knee. The brace 200 includes an upper support region 212 that secures the brace 200 around the thigh above the knee and a lower support region 214 that secures the brace 200 around the lower leg above the ankle. Each of the upper and lower support regions 212 and 214 includes a support enclosed therein, as described herein. The support may be or comprise an elastic material, in place of or in addition to one or more other materials described herein. There is an opening 230 around the knee that allows for air flow and articulation of the joint when wearing the knee brace 200, while reducing or minimizing compression of the knee.

The brace 200 includes two coils 220a/220b within the cover material. Additionally, two coils similar or identical to the coils 220a/220b may be on opposite sides of the brace 200. The length of and/or tension in the coils 220a/220b can be adjusted using the control knob 210 at the top of the brace. Additionally, there may be a control knob similar or identical to the control knob 210 at the bottom of the brace 200, in addition to or in place of the control knob 210 at the top of the brace 200. The coils 220a/220b may be fastened to the brace 200 by stitching, and the wire through the coils 220a/220b may be wrapped around the control knob 210. By turning the control knob 210, the coils 220a/220b can be tightened/shortened or loosened/lengthened to the user's comfort level, and to alleviate pressure on the knee joint and ligaments in the knee joint.

In a further embodiment, the knee brace 200 may include two control knobs 210. One control knob 210 may be on the medial side of the leg and be configured to control the coils 220a/220b on the medial side of the brace 200, and one control knob 210 may be on the lateral side of the leg and be configured to control the coils on the lateral side of the brace 200. Each set of the coils 220a/220b may be anchored to an anchoring eyelet so that the medial and lateral coils 220a/220b may be tightened or adjusted independently of one another. This configuration of the coils allows for maximum control of the knee joint, leading to alleviation of the tension or pain in the knee joint due to compression.

An Exemplary Wrist Brace

Figure 8:
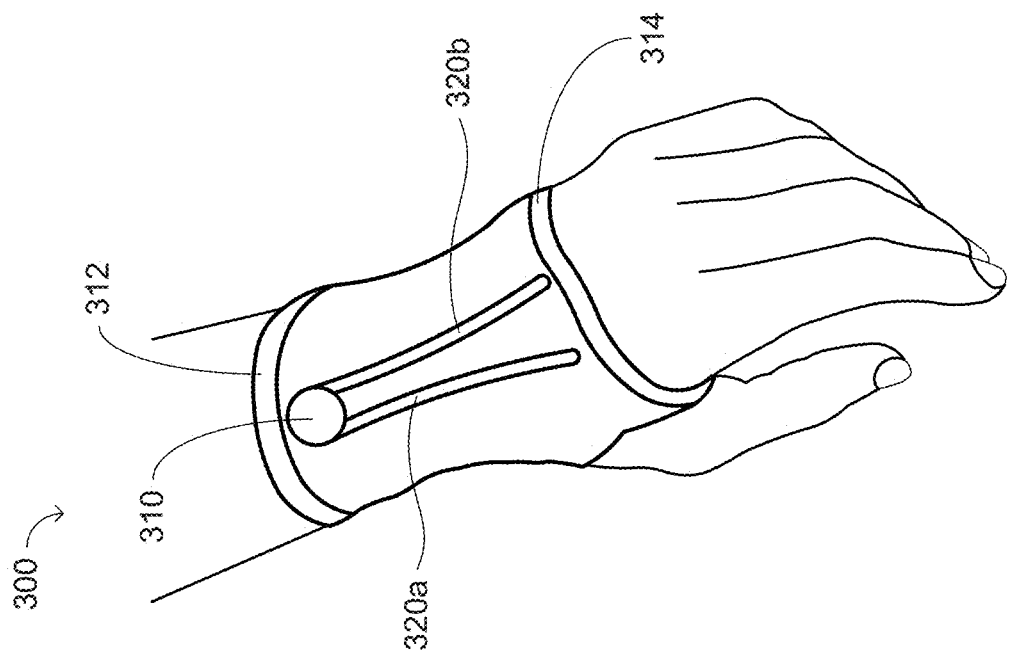
FIG. 8 shows an exemplary wrist brace, in accordance with one or more embodiments of the present invention.

FIG. 8 shows an embodiment of a brace 300 adapted for the wrist. The brace 300 includes an upper support region 312 that secures the brace 300 around the forearm above the wrist and a lower support region 314 that secures the brace 300 around the palm below the wrist. Each of the upper and lower support regions 312 and 314 includes a support enclosed therein, as described herein. The support may be or comprise an elastic material, in place of or in addition to one or more other materials described herein. There may be an opening (not shown) over or around the wrist that allows for air flow and articulation of the joint when wearing the brace 300, while reducing or minimizing compression in the wrist.

The brace 300 includes two coils 320a/320b within the cover material. Additionally, two coils similar or identical to the coils 320a/320b may be on opposite sides of the brace 300. The length of and/or tension in the coils 320a/320b may be adjusted using the control knob 310 at the top or forearm end of the brace 300. Additionally or alternatively, there may be a control knob similar or identical to the control knob 310 at the bottom or hand end of the brace 300. The coils 320a/320b may be fastened to the brace 300 by stitching, and the wire through the coils 320a/320b may be wrapped around the control knob 310. By turning the control knob 310, the coils 320a/320b may be tightened/shortened or loosened/lengthened to the user's comfort level, and to alleviate pressure on the wrist joint and ligaments in the wrist joint.

In a further embodiment, the wrist brace 300 may include two control knobs 310. One control knob 310 may be on the medial side of the arm and be configured to control the coils 320a/320b on the medial side of the brace 300, and one control knob 310 may be on the lateral side of the arm and be configured to control the coils on the lateral side of the brace 300. Alternatively, one control knob 310 may be on the ventral side of the arm and be configured to control the coils 320a/320b on the ventral side of the brace 300, and one control knob 310 may be on the dorsal side of the arm and be configured to control the coils on the dorsal side of the brace 300. Each set of the coils 320a/320b may be anchored to an anchoring eyelet so that the coils 320a/320b may be tightened or adjusted independently of one another. This configuration of the coils allows for maximum control of the wrist joint, leading to alleviation of the tension or pain in the wrist joint due to compression.

An Exemplary Ankle Brace

Figure 9:
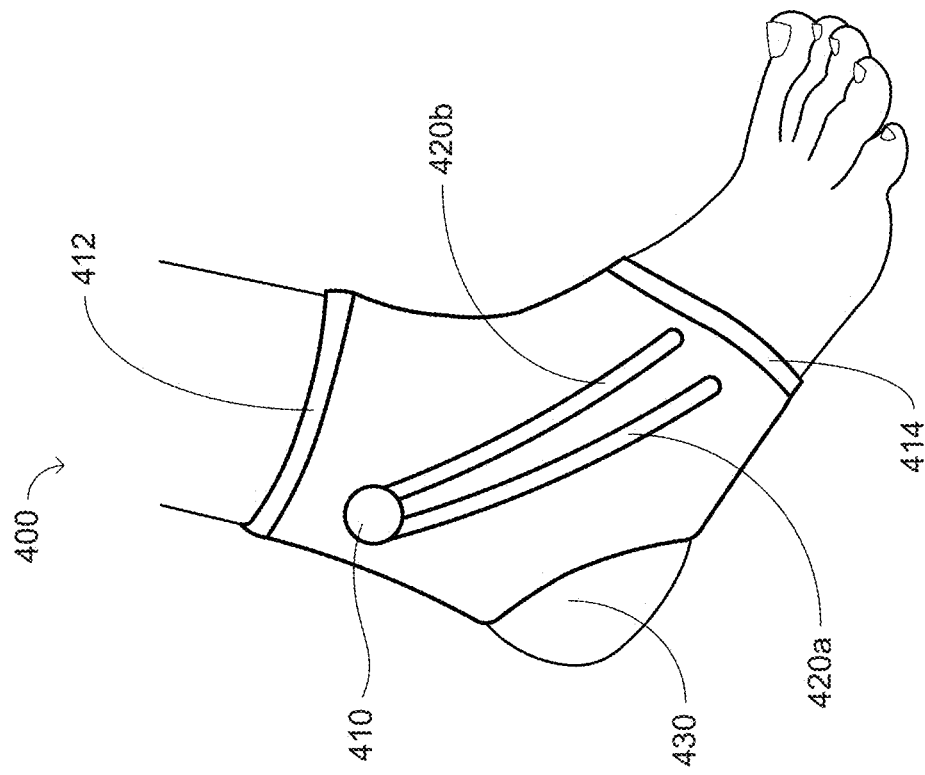
FIG. 9 shows an exemplary ankle brace, in accordance with one or more embodiments of the present invention.

FIG. 9 shows an embodiment of a brace 400 adapted for the ankle. The brace 400 includes an upper support region 412 that secures the brace 400 around the shin above the ankle and a lower support region 414 that secures the brace 400 around the midfoot below the ankle. Each of the upper and lower support regions 412 and 414 includes a support enclosed therein, as described herein. The support may be or comprise an elastic material, in place of or in addition to one or more other materials described herein. There may be an opening 430 around the heel that allows for air flow and articulation of the ankle joint when wearing the brace 400, while reducing or minimizing compression of the ankle.

The brace 400 includes two coils 420a/420b within the cover material, on the lateral side of the brace (as shown). Additionally, two coils similar or identical to the coils 420a/420b may be on an opposite (e.g., medial) side of the brace 400. The length of and/or tension in the coils 420a/420b may be adjusted using the control knob 410 at the top of the brace 400. Additionally or alternatively, there may be a control knob similar or identical to the control knob 410 at the bottom of the brace 400, but a control knob at the foot end of the brace 400 may be disfavored due to a desire of many users to wear footwear such as shoes that may block access to the knob or cause discomfort due to pressure on the control knob. The coils 420a/420b may be fastened to the brace 400 by stitching, and the wire through the coils 420a/420b may be wrapped around the control knob 410. By turning the control knob 410, the coils 420a/420b may be tightened/shortened or loosened/lengthened to the user's comfort level, and to alleviate pressure on the ankle joint and ligaments in the ankle joint.

In a further embodiment, the ankle brace 400 may include two control knobs 410 One control knob 410 may be on the medial side of the shin and be configured to control the coils 420a/420b on the medial side of the brace 400, and one control knob 410 may be on the lateral side of the shin (e.g., as shown) and be configured to control the coils on the lateral side of the brace 400. Each set of the coils 420a/420b may be anchored to an anchoring eyelet so that the medial and lateral coils 420a/420b may be tightened or adjusted independently of one another.

An Exemplary Neck Brace

Figure 10B:
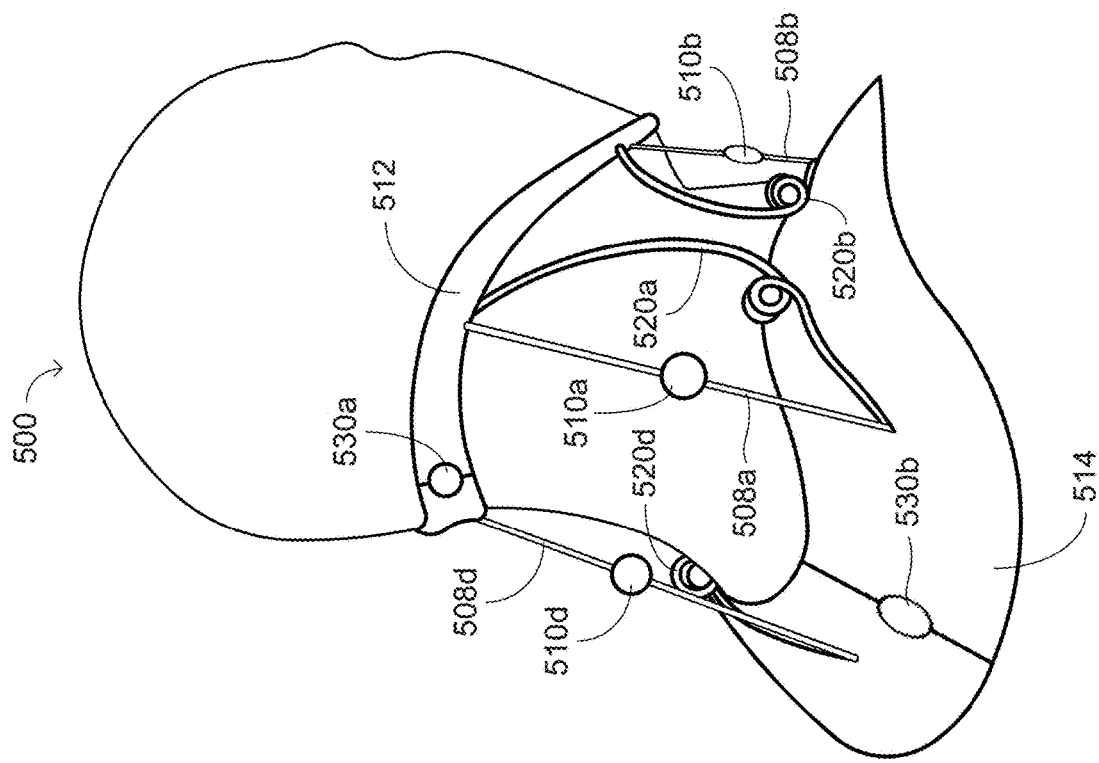
FIGS. 10A-B show an exemplary neck brace, in accordance with one or more embodiments of the present invention.
Figure 10A:
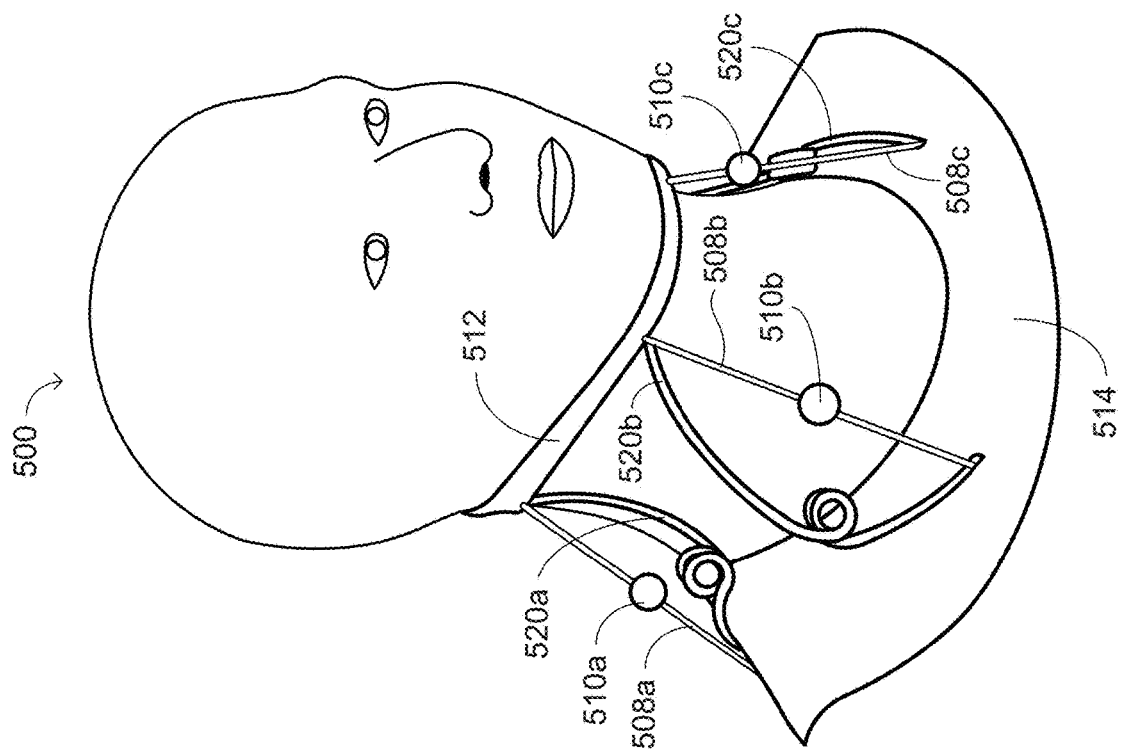

FIGS. 10A and 10B show and embodiment of a brace 500 adapted for the neck. FIG. 10A shows the brace 500 from the front side, and FIG. 10B shows the brace 500 from the back or rear side. For clarity, the cover is omitted. The brace 500 may alleviate compression of the cervical vertebrae (e.g., the vertebrae of the spine in the neck).

The neck brace 500 may include an upper support region having an upper support 512 at or near the top of the neck (e.g., slightly below or at the base of the skull and/or the underside of the chin or lower jaw), and a lower support region having a lower support 514 at or near the bottom of the neck (e.g., slightly above or on the collar bone and/or trapezius muscle). The upper and lower supports 512 and 514 secure the neck brace 500 to the neck of the user. The upper and lower supports 512 and 514 are generally (but not necessarily) separate from each other. In some embodiments, the upper and lower supports 512 and 514 may be attached to a cover and/or substrate of the neck brace 500 by stitching.

The neck brace 500 may include coils or springs 520a-d configured to lengthen the space between the upper and lower supports 512 and 514 and relieve compression between cervical vertebrae. Wires 508a-d may be respectively attached to the coils or springs 520a-d (e.g., ends of the coils or springs 520a-d) and may be controlled by control knobs 510a-d to lengthen or contract the coils or springs 520a-d. In other embodiments, the tension in the coils or springs 520a-d may be controlled by a motor, in turn controlled by a control module and powered by a battery module (e.g., as shown in FIG. 5A). There may be an adjustment knob 530a at an interface of the upper support 512 (e.g., where ends of the upper support 512 are joined or connected) and an additional adjustment knob 530b at an interface of the lower support 514 (e.g., where ends of the lower support 514 are joined or connected). The upper and lower supports 512 and 514 may include a clasping or connecting mechanism (not shown, but which may comprise tabs and/or hooks at one end with matching or mating slots, ridges and/or holes at the other end), and the adjustment knobs 530a-b may tighten or loosen the supports 512 and 514 by controlling the clasping mechanism (e.g., its tightness, looseness, the particular slot, ridge and/or hole into which the matching connector is joined or connected, etc.). Alternatively, the adjustment knobs 530a-b may control wires or other structures (not shown) that circumscribe the supports 512 and 514. Thus, the adjustment knobs 530a-b may tighten or loosen the supports 512 and 514, and thus indirectly control the tension on the springs or coils 520a-d (tightening may reduce the tension, loosening may increase the tension).

A Method of Manufacturing a Brace

In one aspect, the present invention relates to a method of manufacturing a brace as described herein. At a first step, two or more supports configured to contact body parts on opposite sides or ends of one or more joints when the brace is in use may be formed on, placed in, etc., a sleeve, vest, or cover for the brace, generally at the end of the sleeve, vest or cover. The supports may be attached to the brace by stitching, rivets or other fasteners, adhesive, etc. At a second step, one or more force application mechanisms that apply a controllable force to the supports in opposite directions (e.g., a tensile force) to alleviate compression in the one or more joints may be attached to the supports. At a third step (or, alternatively, before the first step), a cover (sleeve, vest, etc.) configured to secure a position of each of the supports in the brace may be formed. The cover, sleeve, vest, etc., may be formed by sewing, assembling, fastening, etc., one or more components thereof to one or more other components thereof. The cover, sleeve, vest, etc., may be further configured to enclose the force application mechanism(s). A cushion or padding covering at least part of each of the supports may be attached to the supports and/or cover. The cushion or padding may be configured to distribute the controllable force across a larger area of the body part(s) contacted by a corresponding support.

The force application mechanism(s) may comprise one or more (e.g., a plurality of) coils or springs coupled to or connected between (i) at least a first one of the supports on a first side or end of the joint(s) and (ii) at least a second one of the supports on a second side or end of the joint(s) opposite from the first side or end. A tension control mechanism configured to change or maintain a tension of each of the plurality of coils may be attached to one, some or all of the coils or springs. The tension control mechanism may comprise one or more wires or cables through the plurality of coils or springs, and a knob or strap operably connected to the wire(s) or cable(s), the knob or strap being configured to control a length of the wire(s) or cable(s). Alternatively, the tension control mechanism may comprise (i) an actuator configured to change or maintain a length of at least one of the coils or springs, and (ii) a motor operably connected to and configured to control a position of the actuator.

Component Manufacturing of a Brace

The following method of manufacturing may be exemplified for making the knee brace, but it is not limited thereto. The methods and materials used in this process may be used to make other embodiments of the invention. The following components may be manufactured using industry-accepted standard techniques and materials. Component configurations may include:

Plastic wheel retainer(s)
Plastic ratchet wheel(s)
Removable plastic turn key(s)
Tensioning wire(s) or ratchet arms
Compression spring(s)

Plastic Wheel Retainer:

The retainer houses the ratchet wheel and may comprise an injection-molded or similarly processed high density polyethylene (HDPE) plastic. It may have a circular or cylindrical shape (e.g., about 10-50 mm in diameter) and a flange at one end thereof (e.g., adapted for attachment to the cover or frame of the brace). In one example, the retainer can be glued or stitched into a recess and/or pocket of the brace.

Plastic Ratchet Wheel:

The ratchet wheel may comprise injection-molded or similarly processed HDPE, similar to the retainer. The outer circumference of the wheel may have several (e.g., 6-10) conical or cylindrical teeth slightly angled in a predetermined direction. The ratchet wheel may further include an inner hole with several (4-5) recessed apertures or grooves. The tensioning wire is attached to the body of the wheel. The wheel may also have two release pins on an outer edge thereof.

Control Knob:

The control knob may comprise injection-molded high-density polypropylene. The knob may have a diameter of 10-40 mm. The knob may include a spoke to which the tension wire is attached (e.g., using an adhesive such as a solder or an epoxy). The face of the knob may include an adhesively-attached or printed label with tick marks that indicate a corresponding level or intensity of actuation or tension in the tension wire. The more the knob is turned, the more compressive the spring becomes, and the lower the force applied to the opposing supports. For example, the tick marks may indicate the level of compression numerically (e.g., where a number such as "1" indicates the greatest force, and a number such as "5" or "10" indicates the least force).

Plastic Turn-Key:

The turn-key may also comprise injection-molded or similarly processed HDPE. The key generally consists of a single molded piece, and may have a hollow body and/or a key head with two or more flanged wings. The key body may have a number of (e.g., 4-5) abutments that run longitudinally along the sides of the body. The number and dimensions of the abutments generally complement the grooves or apertures in the inner hole (e.g., the "keyhole") of the ratchet wheel so that when the key is inserted into the hole in the ratchet wheel, the abutments mate with and/or sit flush against the grooves or apertures. Upon correct insertion of the key body into the ratchet wheel, the operator or user can then torque the key to the desired level of tension.

In an alternative method of construction shown in FIGS. 11A-B, a lever 630 attached to the ratchet wheel behind control knob 610 can apply a force to two bars or counter-supports 640*a-b* attached to bushings or shoulder washers 635*a-d* at inner ends of the springs or coils 620*a-d*. The outer ends of the springs or coils 620*a-d* are connected to the brace supports (not shown). The springs or coils 620*a-d* may be enclosed in sleeves in the brace. There may be only a single spring or coil 620 attached or coupled to each bar 640*a-b*, or more than two springs or coils 620. The bars or counter-supports 640*a-b* have a long axis that is perpendicular to the axis of the springs or coils 620*a-d*. The lever 630 may be fixedly attached at the center to the control knob 610 (e.g., via solder, a fastener, or integration such as injection molding) and rotatingly attached at each end to one of the bars or counter-supports 640*a-b* (e.g., with a set screw, peg-and-hone connection, rivet, etc.). In the neutral position (FIG. 11A), the bars or counter-supports 640*a-b* lie horizontally against one another. As the knob 610 is turned, the lever 630 drives the two bars or counter-supports 640*a-b* apart (FIG. 11B), compressing the spring on either side of the joint against the brace support and lessening the pressure in and around the joint. The longer the lever 630, the greater the compressive force. However, the distance by which the springs 620*a-d* compress as the control knob 610 is turned may change in proportion to the sine of the angle of the lever 630 relative to the neutral position of the bars 640*a-b*.

Tensioning Wire:

The tensioning wire can be attached directly to the ratchet wheel. The wire preferably has a minimum diameter of 0.375 mm. The wire thickness may be determined by the force needed to contract or expand the spring(s) or coil(s). Ideally, the wire can be attached to the ratchet wheel with either a standard epoxy or a fastener.

Compression Spring:

The compression spring or coil may have a minimum compressive force of 1 kg. The spring or coil should be completely or substantially completely restorative (e.g., compress or expand and return to a nominal, uncompressed position).

An Exemplary Method of Supporting and/or Stabilizing One or More Joints

In yet another aspect, the present invention relates to a method of supporting and/or stabilizing one or more joints (e.g., in a human or animal body). At a first step, a brace may be secured around the joint(s), the brace comprising (i) two or more supports configured to contact parts of the body on opposite sides or ends of the joint(s) when the brace is in use and (ii) one or more force application mechanisms that apply a controllable force to the supports in opposite directions to alleviate compression in the joint(s). At a second step, a sufficient force may be applied to the supports using the force application mechanism(s) to alleviate the compression in the joint(s). The brace may further comprise a cover configured to enclose the supports and/or force application mechanism(s). The method may further include distributing the controllable force across an area of the body part(s) contacted by a corresponding support with a cushion or padding covering at least part of the support. The force application mechanism(s) may comprise one or more (e.g., a plurality of) coils as described above. A tension of each of the coils may be changed or maintained with a tension control mechanism as described herein.

CONCLUSION

The present invention relates to a brace that advantageously provides greater relief to targeted joint(s) through the use of coils, springs or other mechanisms that apply opposing forces to supports on opposite sides of the targeted joint(s), and that can be adjusted (e.g., by the user) to achieve greater comfort. The present brace is generally less bulky than traditional braces, enabling daily use during a multitude of activities. Individuals with chronic back pain, athletes, and those who spend long hours at a desk or driving a vehicle may find long-term relief from use of the present invention.

The foregoing descriptions of specific embodiments of the present invention have been presented for purposes of illustration and description. They are not intended to be exhaustive or to limit the invention to the precise forms disclosed, and obviously many modifications and variations are possible in light of the above teaching. The embodiments were chosen and described in order to best explain the principles of the invention and its practical application, to thereby enable others skilled in the art to best utilize the invention and various embodiments with various modifications as are suited to the particular use contemplated.

We claim:

1. An apparatus, comprising:
    two or more supports, configured to contact body parts on opposite sides or ends of one or more joints when the apparatus is in use;
    one or more force application mechanisms that apply a controllable force to the two or more supports in opposite directions to alleviate compression in the one or more joints, wherein the one or more force application mechanisms comprises:
        a plurality of springs or coils coupled to or connected between (i) at least a first one of the two or more supports on a first side or end of the one or more joints and (ii) at least a second one of the two or more supports on a second side or end of the one or more joints opposite from the first side or end, and
        a tension control mechanism configured to change or maintain a tension of each of the plurality of springs or coils such that (i) increasing a tension in the springs or coils decreases a distance between the supports on the opposite sides or ends of the one or more joints and reduces a force on the body parts in contact with the supports on the opposite sides or ends of the one or more joints, and (ii) decreasing the tension in the springs or coils increases the distance between the supports on the opposite sides or ends of the one or more joints and increases the force on the body parts in contact with the supports on the opposite sides or ends of the one or more joints, wherein the tension control mechanism comprises:
            a first wire or cable through a first subset of the plurality of springs or coils;
            a second wire or cable through a second subset of the plurality of springs or coils, at least one of the springs or coils in the second subset being different from the springs or coils in the first subset; and
            a first actuator operably connected to the first wire or cable, the first actuator being configured to control a length of the first wire or cable; and
            a second actuator operably connected to the second wire or cable, the second actuator being configured to control a length of the second wire or cable; and
        a cover configured to (i) secure a position of each of the two or more supports in the apparatus and (ii) enclose the plurality of springs or coils and the first and second wires or cables.

2. The apparatus of claim 1, wherein each of the first and second actuators comprises:
    a knob, clamp or strap operably connected to the one or more wires or cables, the knob, clamp or strap being configured to control the length of the corresponding first or second wire or cable.

3. The apparatus of claim 1, wherein the tension control mechanism further comprises:
    a motor operably connected to and configured to control a position of at least one of the first and second actuators.

4. The apparatus of claim 3, further comprising a microcontroller configured to control the motor.

5. The apparatus of claim 4, further comprising a memory operably connected to the microcontroller, wherein the memory stores a program configured to operate the motor.

6. The apparatus of claim 4, further comprising a wireless receiver operably connected to the microcontroller, configured to receive one or more instructions from a user-operated wireless transmitter.

7. The apparatus of claim 3, further comprising a battery configured to provide power to the motor.

8. The apparatus of claim 1, further comprising a cushion or padding covering at least part of one of the two or more supports, the cushion or padding being configured to distribute the controllable force across an area of the body part(s) contacted by a corresponding support.

9. The apparatus of claim 1, further comprising one or more cushions or pads covering at least part of each of the two or more supports.

10. The apparatus of claim 1, wherein the cover is further configured to enclose the two or more supports.

11. The apparatus of claim 10, wherein the one or more joints is vertebrae in a spine, the two or more supports contact (i) under left and right arms and (ii) above left and right hips, and the plurality of springs or coils are on left and right sides and on front and back sides of a torso.

12. The apparatus of claim 8, wherein the cushion or padding is between the one of the two or more supports and the cover.

13. An apparatus, comprising:
    two or more supports, configured to contact body parts on opposite sides or ends of one or more joints when the brace is in use;
    one or more force application mechanisms that apply a controllable force to the two or more supports in opposite directions to alleviate compression in the one or more joints, comprising:
        a plurality of springs or coils coupled to or connected between (i) at least a first one of the two or more supports on a first side or end of the one or more joints and (ii) at least a second one of the two or more supports on a second side or end of the one or more joints opposite from the first side or end, and
        a tension control mechanism configured to change or maintain a tension of each of the plurality of springs or coils, wherein the tension control mechanism comprises:

a first wire or cable through a first subset of the plurality of springs or coils;
  a second wire or cable through a second subset of the plurality of springs or coils, at least one of the springs or coils in the second subset being different from the springs or coils in the first subset; and
  a first actuator operably connected to the first wire or cable, the first actuator being configured to control a length of the first wire or cable; and
  a second actuator operably connected to the second wire or cable, the second actuator being configured to control a length of the second wire or cable; and
 a cover configured to (i) secure a position of each of the two or more supports in the apparatus and (ii) enclose the plurality of springs or coils and the first and second wires or cables, wherein the one or more force application mechanisms are flexible when enclosed by the cover.

14. The apparatus of claim 13, further comprising a cushion or padding covering at least part of each of the two or more supports, the cushion or padding being configured to distribute the controllable force across a larger area of the body part(s) contacted by a corresponding one of the two or more supports.

15. The apparatus of claim 13, wherein increasing a tension in the springs or coils reduces a force on the body parts in contact with the supports on the opposite sides or ends of the one or more joints, and decreasing the tension in the springs or coils increases the force on the body parts in contact with the supports on the opposite sides or ends of the one or more joints.

16. The apparatus of claim 13, wherein the cover encloses the two or more supports.

17. The apparatus of claim 13, wherein the one or more joints is vertebrae in a spine, the two or more supports contact (i) under left and right arms and (ii) above left and right hips, and the plurality of springs or coils are on left and right sides and on front and back sides of a torso.

* * * * *